United States Patent
Wan et al.

(10) Patent No.: US 10,332,250 B2
(45) Date of Patent: Jun. 25, 2019

(54) THREE-DIMENSIONAL CAVITATION QUANTITATIVE IMAGING METHOD FOR MICROSECOND-RESOLUTION CAVITATION SPATIAL-TEMPORAL DISTRIBUTION

(71) Applicant: XI'AN JIAOTONG UNIVERSITY, Xi'an, Shaanxi (CN)

(72) Inventors: Mingxi Wan, Shaanxi (CN); Ting Ding, Shaanxi (CN); Hong Hu, Shaanxi (CN); Miao Yang, Shaanxi (CN); Shifang Guo, Shaanxi (CN)

(73) Assignee: XI'AN JIAOTONG UNIVERSITY, Xi'an, Shaanxi (CN)

( * ) Notice: Subject to any disclaimer, the term of this patent is extended or adjusted under 35 U.S.C. 154(b) by 275 days.

(21) Appl. No.: 15/115,682

(22) PCT Filed: Jan. 26, 2015

(86) PCT No.: PCT/CN2015/071540
§ 371 (c)(1),
(2) Date: Jul. 31, 2016

(87) PCT Pub. No.: WO2016/101382
PCT Pub. Date: Jun. 30, 2016

(65) Prior Publication Data
US 2017/0011508 A1    Jan. 12, 2017

(30) Foreign Application Priority Data
Dec. 27, 2014    (CN) .......................... 2014 1 0834392

(51) Int. Cl.
*G06T 7/00* (2017.01)
*G06T 7/60* (2017.01)
(Continued)

(52) U.S. Cl.
CPC .......... *G06T 7/0012* (2013.01); *G01N 29/02* (2013.01); *G01N 29/0654* (2013.01);
(Continued)

(58) Field of Classification Search
CPC ... G01N 2291/02433; G01N 2291/106; G01N 29/02; G01N 29/0654; G01N 29/265;
(Continued)

(56) References Cited

U.S. PATENT DOCUMENTS

2016/0151618 A1 * 6/2016 Powers .................... A61N 7/00
600/439

* cited by examiner

*Primary Examiner* — Alison Slater (57) ABSTRACT

A three-dimensional cavitation quantitative imaging method for a microsecond-resolution cavitation spatial-temporal distribution includes steps of: after each wide beam detection, moving an array transducer by one unit; waiting until the cavitation nuclei distribution backs to an initial state, then detecting the cavitation by the wide beam detection with same cavitation energy incitation, so as to obtain a spatial series of two-dimensional cavitation raw radio frequency data corresponding to different placing positions of the array transducer; then changing the cavitation energy source duration, time delays between energy source incitation and the wide beam transmitted by the array transducer, and time delays between the pulsating pump and energy source incitation, so as to obtain a temporal series of two-dimensional cavitation raw radio frequency data; and then obtaining a microsecond-resolution three-dimensional cavitation spatial-temporal distribution image and a cavitation micro bubble concentration quantitative Nakagami parametric image.

6 Claims, 9 Drawing Sheets

(51) Int. Cl.
*G06T 5/00* (2006.01)
*G01N 29/02* (2006.01)
*G06T 11/00* (2006.01)
*G01N 29/06* (2006.01)
*G01N 29/265* (2006.01)

(52) U.S. Cl.
CPC ............ *G01N 29/265* (2013.01); *G06T 5/00* (2013.01); *G06T 7/60* (2013.01); *G06T 11/008* (2013.01); *G01N 2291/02433* (2013.01); *G01N 2291/106* (2013.01); *G06T 2200/04* (2013.01); *G06T 2207/10136* (2013.01); *G06T 2207/20182* (2013.01)

(58) Field of Classification Search
CPC ....... G06T 2200/04; G06T 2207/10136; G06T 2207/20182
See application file for complete search history.

THREE-DIMENSIONAL CAVITATION QUANTITATIVE IMAGING METHOD FOR MICROSECOND-RESOLUTION CAVITATION SPATIAL-TEMPORAL DISTRIBUTION

CROSS REFERENCE OF RELATED APPLICATION

This is a U.S. National Stage under 35 U.S.C. 371 of the International Application PCT/CN2015/071540, filed Jan. 26, 2015, which claims priority under 35 U.S.C. 119(a-d) to CN 201410834392.1, filed Dec. 27, 2014.

BACKGROUND OF THE PRESENT INVENTION

Field of Invention

The present invention relates to cavitation physics and ultrasound imaging technologies, wherein a method of the present invention combines array transducer plane-by-plane wide beam cavitation detection, wide beam minimum variance adaptive beamforming, and Nakagami parametric imaging algorithms, so as to achieve microsecond-resolution cavitation three-dimensional spatial-temporal distribution imaging and cavitation bubble concentration quantitative imaging under conditions of a steady-state free field and a pulsating flow.

Description of Related Arts

Cavitation refers to a series of kinetic processes such as micro nucleate oscillation, growth, shrinkage and even collapse, which is caused by activating cavitation nucleus in liquid by external energy (heat/force). In biomedical field, the cavitation is a main mechanism for drug delivery, gene transfection, extracorporeal lithotripsy, thrombolysis, hemostasis, hyperthermia, thermal ablation of tumors, etc. Cavitation processes comprises the following phases: cavitation nucleation, cavitation bubble linear and nonlinear vibration, cavitation bubble growth, rapidly shrinking to collapse, and cavitation bubble dissipating. The cavitation is divided into steady-state ones featuring non-inertial cavitation, and transient-state ones featuring inertial cavitation. In a liquid medium, a minimum cavitation energy value is called a cavitation starting threshold, which depends on the static pressure, initial temperature and structural state of the liquid medium and diverse cavitation nuclei externally added into the liquid. Therefore, the cavitation generated in the liquid medium has certain randomness, but with the same environments and energy, shapes and distributions of cavitation bubble clouds are repeatable. Conventionally, in order to better study cavitation generation mechanisms based on different media, so as to better control and use the cavitation, effective cavitation detection and imaging methods should be researched.

Conventionally cavitation detection and imaging are mainly achieved by optical and acoustic methods. Optical detection imaging comprises high-speed/ultra-high-speed photography, sonoluminescence and sonochemiluminescence, which is able to photograph and observe cavitation bubble behavior and spatial-temporal dynamic characteristics. Advantages thereof are being intuitive, good synchronization, and high time resolution. Shortcomings are that on one hand, media translucent is highly demanded and the optical detection imaging is not suitable for in-situ study; on the other hand, images obtained are information superimposed along an optical penetration direction. Acoustic detection method is based on sound information about cavitation processes or cavitation micro bubbles, such as harmonics, sub harmonics, super harmonic and broadband noise, wherein passive cavitation detection (PCD) and active cavitation detection (ACD) are most widely used. The PCD passively receives acoustic scattering signals generated by the cavitation through a transducer, and the ACD detects potential cavitation areas with low-voltage pulse echoes. However, both the PCD and the ACD generally use a single element transducer, which are not able to provide spatial distribution of cavitation micro bubble due to limited space detection areas.

Based on the PCD and the ACD, a two-dimensional array transducer is used as a cavitation detection transducer, resulting in development of passive cavitation imaging (PCI) and active cavitation imaging (ACI). Due to transient characteristics, vibration, collapse and dissipation of ultrasonic cavitation micro bubbles only last for a few microseconds. Therefore, the cavitation imaging method requires microsecond time resolution. Meanwhile, for the cavitation transient characteristics, it is necessary to obtain spatial-temporal distribution of cavitation micro bubble, comprising sequence spatial-temporal cavitation distributions of different cavitation energy source actuation durations and cavitation dissipating times. The PCI passively receives through an array transducer and then obtains cavitation bubble two-dimensional distribution through channel signal source reconstruction, wherein a reconstruction algorithm is complex and spatial resolution is not high. The ACI comprises conventional B-mode imaging and ultra-fast active cavitation imaging methods. Since the B-mode imaging is achieved through line by line scanning, time differences exist between different scanning lines of the same frame, and a time resolution is not at a microsecond level. The ultra-fast active cavitation imaging launches a plane wave, so sensitivity and lateral resolution thereof need to be improved, and a time resolution is a few hundred microseconds, which is not able to meet requirements of studying cavitation transient distribution.

Based on the cavitation imaging, cavitation bubble characteristics need to be identified, comprising cavitation quantifying, and cavitation size and concentration distributions. Conventionally, cavitation quantification methods mainly adopt inertial cavitation doses and non-inertial cavitation doses, which calculate a root mean square value of broadband noise within a specific frequency band or a sub harmonic amplitude for obtaining a relative measure of cavitation intensity, so as to respectively measure the relative intensity of transient-state and steady-state cavitation. However, for one-dimensional radio frequency data collected by the PCD, such quantification methods cannot describe cavitation intensity distribution. Conventional cavitation concentration detection methods comprise a laser phase Doppler method which is focused on size distributions of cavitation bubble, but concentration distributions of cavitation bubble at different spatial locations have not been searched, resulting in no spatial information provided.

Conventionally, cavitation detection and imaging methods are limited to one-dimension and two-dimension. Actually, distribution areas of cavitation bubbles are throughout a whole focal region or even greater. Furthermore, in clinical applications such as focused ultrasound therapy, there may be other organization media in an acoustic propagation path, in such a manner that sound field distribution changes will lead to asymmetry. Therefore, it is necessary to develop microsecond-resolution cavitation three-dimensional spatial-temporal distribution imaging and cavitation bubble concentration quantitative imaging methods. In addition, there are fewer researches on cavitation under flow conditions, especially pulsating flow conditions. However, blood flow of a human body is pulsating flow, so it is necessary to study three-dimensional spatial-temporal cavitation distribution based on such conditions, especially three-dimensional cavitation distribution at different time points within a pulsating flow cycle.

SUMMARY OF THE PRESENT INVENTION

For overcoming defects of the above conventional technologies and necessity of three-dimensional cavitation quantitative imaging for a microsecond-resolution cavitation spatial-temporal distribution, an object of the present invention is to provide a three-dimensional cavitation quantitative imaging method for a microsecond-resolution cavitation spatial-temporal distribution under conditions comprising a static-state free field and a pulsating flow.

Accordingly, in order to accomplish the above object, the present invention provides:

a three-dimensional cavitation imaging and cavitation concentration quantitative imaging method for a microsecond-resolution cavitation spatial-temporal distribution under a static-state free field, whose principles are as follows:

under the static-state free field, using a plane-by-plane wide beam for detecting cavitation, which overcomes a disadvantage of de-synchrony space in a same frame of cavitation image; after each wide beam detection, moving an array transducer by one unit; waiting until a medium cavitation nuclei distribution backs to an initial state without effects of a cavitation energy source, then detecting the cavitation by the wide beam detection with same cavitation energy incitation, so as to obtain a two-dimensional cavitation original radio frequency data collection corresponding to different placing positions of the array transducer; and obtaining a three-dimensional cavitation image and a cavitation micro bubble concentration quantitative three-dimensional image for the microsecond-resolution cavitation spatial-temporal distribution under the static-state free field by combining wide beam minimum variance adaptive beamforming (Synnevag, J. F., A. Austeng, et al. (2007). "Adaptive beamforming applied to medical ultrasound imaging." Ieee Transactions on Ultrasonics Ferroelectrics and Frequency Control 54(8): 1606-1613), Nakagami parametric imaging, and a three-dimensional reconstruction algorithm.

Step 1: using the plane-by-plane wide beam for detecting the cavitation, wherein the cavitation is generated by a source energy whose temperature or pressure is continuously adjustable; and acquiring a cavitation signal; wherein a cavitation generator comprises an energy source for generating an energy field and a synchronous signal generator for controlling a time sequence; a cavitation detector comprises the array transducer which is programmable and transmits the wide beam, and a parallel channel data acquisition and storage unit; wherein the synchronous signal generator generates a synchronous signal so as to respectively control the energy source and the array transducer; the energy source generates continuously adjustable energy which incites the cavitation; the array transducer transmits the wide beam for detecting the cavitation, and a cavitation echo signal obtained is acquired and stored by the parallel channel data acquisition and storage unit; waiting until a medium cavitation nuclei distribution backs to an initial state, controlling with a three-dimensional mechanical scanner for moving the array transducer by one unit along a direction perpendicular to a placing direction of the array transducer, generating the cavitation again by cavitation energy source incitation with same parameters, and meanwhile transmitting the wide beam by the array transducer for acquiring cavitation radio frequency data; repeating the above processes for obtaining a two-dimensional cavitation distribution image original radio frequency data collection corresponding to different placing positions along the direction perpendicular to the placing direction of the array transducer with same cavitation energy source parameters.

Step 2: processing the distribution image original radio frequency data collection with the wide beam minimum variance adaptive beamforming, so as to obtain a two-dimensional cavitation distribution collection at the different placing positions of the array transducer along the direction perpendicular to the placing direction of the array transducer; wherein specifically, selecting a certain placing position as a target point in a two-dimensional cavitation imaging area, calculating effective aperture and time delay according to a target point position for obtaining a channel signal after receive-focusing the target point; then processing the channel signal with the wide beam minimum variance adaptive beamforming, for optimized amplitude variation and output of the channel signal at the target point; traversing all target points in the two-dimensional cavitation imaging area for obtaining two-dimensional cavitation beamformed radio frequency data at the placing position; using the above processes for traversing all the placing positions for obtaining a two-dimensional cavitation distribution radio frequency data collection; finally, using a radio frequency imaging algorithm for two-dimensional cavitation radio frequency imaging, so as to obtain a two-dimensional distribution image collection with high resolutions and high signal-noise ratios.

Step 3: on one hand, processing the two-dimensional cavitation distribution image collection corresponding to the different placing positions along the direction perpendicular to the placing direction, which is obtained in the step 2, with three-dimensional reconstruction, for obtaining a three-dimensional cavitation distribution image; on the other hand, enveloping the two-dimensional cavitation beamformed radio frequency data obtained in the step 2 before Nakagami parametric extraction for obtaining a cavitation concentration distribution; wherein specifically, using a three-dimensional reconstruction algorithm for three-dimensional-displaying the two-dimensional cavitation distribution image collection corresponding to different placing positions; firstly processing the two-dimensional cavitation beamformed radio frequency data with Nakagami parametric calculation for obtaining a two-dimensional cavitation concentration quantitative image collection corresponding to different placing positions, and secondly using the three-dimensional reconstruction algorithm for three-dimensional-displaying the cavitation concentration quantitative image.

Step 4: changing parameters and media of the energy source for generating the cavitation, and repeating the step 1 to the step 3, so as to obtain cavitation and cavitation concentration quantitative three-dimensional images under different conditions; wherein by changing a cavitation energy incitation duration, a time resolution is up to a few microseconds, and by repeating the step 1 to the step 3, time-related cavitation and cavitation concentration quantitative three-dimensional images are obtained; by changing a cavitation energy value and repeating the step 1 to the step 3, energy-related cavitation and cavitation concentration quantitative three-dimensional images are obtained; by changing a time delay between the cavitation energy incitation and transmitting the wide beam by the array transducer as well as repeating the step 1 to the step 3, timerelated-dissipating cavitation and cavitation concentration quantitative three-dimensional images are obtained; by changing a cavitation energy medium and repeating the step 1 to the step 3, medium-related cavitation and cavitation concentration quantitative three-dimensional images are obtained.

In the step 3, the Nakagami parametric extraction comprises steps of:

1) de-noising two-dimensional cavitation radio frequency data rf:

a) selecting a background signal area with a certain size, and calculating an average energy P of the background signal area;

b) respectively superimposing a first random Gauss white noise $n_1$ and a second random Gauss white noise $n_2$, both having the average energy P, on the rf, so as to obtain $S_1$ and $S_2$; and c) calculating a correlation coefficient of the $S_1$ and the $S_2$ and giving a threshold Th; threshold-processing the correlation coefficient and then weighting with the rf for obtaining $rf_{denoise}$ as follows, wherein corrcoef $(S_1,S_2)$ coefficient of the $S_1$ and the $S_2$;

$$rf_{denoise} = \begin{cases} rf, & corrcoef(S_1, S_2) > Th \\ 0, & corrcoef(S_1, S_2) \le Th \end{cases} \quad (1)$$

2) processing the de-noised $rf_{denoise}$ with Hilbert demodulation, so as to obtain an envelope signal R; and 3) calculating a Nakagami parameter:

$$m = \frac{[E(R^2)]^2}{E[R^2 - E(R^2)]^2} \quad (3)$$

wherein E($\square$) represents a statistical mean.

A three-dimensional cavitation imaging and cavitation concentration quantitative imaging method for a microsecond-resolution cavitation spatial-temporal distribution under a pulsating flow condition has principles as follows. Because a time scale of a pulsating cycle is much greater than that of a transient-state change, a cavitation nuclei distribution will back to an initial state after waiting for times of the pulsating cycle. When detecting the cavitation by the plane-by-plane wide beam, a two-dimensional cavitation distribution image original radio frequency data collection at different time points within the pulsating cycle is obtained by changing a time delay between a pulsating pump and the cavitation energy source; and a two-dimensional cavitation distribution image original radio frequency data collection at different placing positions is obtained by changing the placing position of the array transducer. Then by combining the wide beam minimum variance adaptive beamforming, the Nakagami parametric imaging, and the three-dimensional reconstruction algorithm, a three-dimensional cavitation image and a cavitation micro bubble concentration quantitative image for the microsecond-resolution cavitation spatial-temporal distribution under the pulsating flow condition are obtained. The method comprises steps as follow.

Step 1: using an artificial vascular tissue phantom to imitate vascular and surrounding tissues, connecting both sides of a pipeline thereof to hose pipes, and connecting to a pulsating pump; connecting the artificial vascular tissue phantom to a three-dimensional mechanical scanner, placing in a cavitation source effective area by three-dimensional movements, and generating cavitation inside the pipeline of the artificial vascular tissue phantom.

Step 2: testing different flow patterns under different pulsating pump parameters: specifically, using pulsating liquid as a normal saline contrast agent micro bubble solution, setting the pulsating pump parameters comprising pulsating times per minute and a flow rate, observing a Doppler spectrum and recording a pulsating cycle and patterns, and flowing deionized water in the pipeline for washing away the normal saline contrast agent micro bubble solution.

Step 3: using the array plane-by-plane wide beam for detecting the cavitation, generating the cavitation with a continuously adjustable source energy temperature of pressure, and acquiring a cavitation signal: specifically, setting the pulsating cycle and the flow rate, and accordingly editing a time sequence; controlling a pulsating flow device, a cavitation source device and a cavitation signal detector; wherein the pulsating flow device comprises a pulsating pump for generating a pulsating flow, the artificial vascular tissue phantom, and a synchronous signal generator controlling the artificial vascular tissue phantom; the cavitation source device comprises an energy source for generating an energy field and a synchronous signal generator for controlling the time sequence; the cavitation detector comprises the array transducer which is programmable and transmits the wide beam, and a parallel channel data acquisition and storage unit; wherein the synchronous signal generator generates a synchronous signal so as to respectively control the pulsating pump, the energy source and the array transducer; the pulsating pump enables liquid to flow into or out of the artificial vascular tissue phantom with certain pulsating cycle and flow rate; the energy source generates continuously adjustable energy which incites the cavitation; the array transducer transmits the wide beam for detecting the cavitation, and a cavitation echo signal obtained is acquired and stored by the parallel channel data acquisition and storage unit.

Step 4: keeping an array transducer position, changing a time delay between pulsating pump trigger and cavitation energy source incitation, and repeating the step 3, so as to get a two-dimensional cavitation distribution image original radio frequency data collection corresponding to different time points within the pulsation cycle: specifically, fixing the array transducer, according to a pulsating cycle and a pulsating pattern recorded by a pulsating flow Doppler spectrum, changing a time delay between the pulsating pump and the energy source, waiting until a medium cavitation nuclei distribution backs to an initial state, and repeating the step 3, in such a manner that the two-dimensional cavitation distribution image original radio frequency data corresponding to the different time points within the pulsation cycle are obtained.

Step 5: changing the array transducer position, and repeating steps 3 and 4 for obtaining a two-dimensional cavitation distribution image original radio frequency data collection corresponding to different positions and different time points within the pulsating cycle: specifically, controlling with a three-dimensional mechanical scanner for moving the array transducer by one unit along a direction perpendicular to a placing direction of the array transducer, waiting until a medium cavitation nuclei distribution backs to an initial state, generating the cavitation again by cavitation energy source incitation with same parameters, meanwhile transmitting the wide beam by the array transducer for acquiring cavitation radio frequency data, and repeating the above processes for obtaining a two-dimensional cavitation distribution image original radio frequency data collection corresponding to different placing positions along the direction perpendicular to the placing direction of the array transducer with same cavitation energy source parameters; with different placing positions, repeating the step 4, so as to obtain two-dimensional cavitation distribution image original radio frequency data corresponding to different time points within the pulsating cycle at the placing position.

Step 6: processing the distribution image original radio frequency data collection with the wide beam minimum variance adaptive beamforming, so as to obtain a two-dimensional cavitation distribution collection at the different placing positions of the array transducer along the direction perpendicular to the placing direction of the array transducer; wherein specifically, selecting a certain placing position as a target point in a two-dimensional cavitation imaging area, calculating effective aperture and time delay according to a target point position for obtaining a channel signal after receive-focusing the target point; then processing the channel signal with the wide beam minimum variance adaptive beamforming, for optimized amplitude variation and output of the channel signal at the target point; traversing all target points in the two-dimensional cavitation imaging area for obtaining two-dimensional cavitation beamformed radio frequency data at the placing position; using the above processes for traversing all the placing positions for obtaining a two-dimensional cavitation distribution radio frequency data collection; finally, using a radio frequency imaging algorithm for two-dimensional cavitation radio frequency imaging, so as to obtain a two-dimensional distribution image collection with high resolutions and high signal-noise ratios.

Step 7: on one hand, processing the two-dimensional cavitation distribution image collection corresponding to the different placing positions along the direction perpendicular to the placing direction, which is obtained in the step 2, with three-dimensional reconstruction, for obtaining a three-dimensional cavitation distribution image; on the other hand, enveloping the two-dimensional cavitation beamformed radio frequency data obtained in the step 2 before Nakagami parametric extraction for obtaining a cavitation concentration distribution; wherein specifically, using a three-dimensional reconstruction algorithm for three-dimensional-displaying the two-dimensional cavitation distribution image collection corresponding to different placing positions; firstly processing the two-dimensional cavitation beamformed radio frequency data with Nakagami parametric calculation for obtaining a two-dimentional cavitation concentration quantitative image collection corresponding to different placing positions, and secondly using the three-dimensional reconstruction algorithm for three-dimensional-displaying the cavitation concentration quantitative image.

Step 8: changing parameters and media of the energy source for generating the cavitation, and repeating the step 3 to the step 7, so as to obtain cavitation and cavitation concentration quantitative three-dimensional images with different parameters under the pulsating flow condition; wherein by changing a cavitation energy incitation duration, a time resolution is up to a few microseconds, and by repeating the step 3 to the step 7, time-related cavitation and cavitation concentration quantitative three-dimensional images under the pulsating flow condition are obtained; by changing a cavitation energy value and repeating the step 3 to the step 7, energy-related cavitation and cavitation concentration quantitative three-dimensional images under the pulsating flow condition are obtained; by changing a time delay between the cavitation energy incitation and transmitting the wide beam by the array transducer as well as repeating the step 3 to the step 7, time-related-dissipating cavitation and cavitation concentration quantitative three-dimensional images under the pulsating flow condition are obtained; by changing a cavitation energy medium and repeating the step 3 to the step 7, medium-related cavitation and cavitation concentration quantitative three-dimensional images under the pulsating flow condition are obtained.

According to cavitation spatial-temporal distribution researches under static-state free field and pulsating flow conditions, the present invention firstly uses the array plane-by-plane wide beam for detecting the cavitation, and acquires the two-dimensional cavitation distribution image original image data collection at different placing positions along the direction perpendicular to the placing direction of the array transducer. Then the wide beam minimum variance adaptive beamforming is used for obtaining two-dimensional cavitation distribution sequence images at different placing positions, and the Nakagami parametric algorithm is used for extracting quantitative images which represents cavitation densities. Finally, the three-dimensional reconstruction algorithm is used for obtaining the three-dimensional quantitative image of the microsecond-resolution cavitation spatial-temporal distribution. By changing the cavitation source energy incitation duration and a time delay between the cavitation source energy incitation and the wide beam detection, time sequence cavitation images are obtained; and by changing the energy source parameters and the medium, cavitation and cavitation concentration quantitative three-dimensional sequence images are obtained. The method has a potential to be a three-dimensional cavitation imaging standard method which is similar to acoustic field measurement.

Compared with the conventional technologies, the present invention has advantages as follows:

compared with the conventional technologies, the present invention firstly uses the plane-by-plane wide beam for detecting the cavitation, which has a microsecond time resolution, and is able to observe cavitation bubble ground transient-state distributions; secondly, the cavitation images obtained by the wide beam minimum variance adaptive beamforming have a relatively high space resolution and signal-noise ratio; then the cavitation micro bubble concentration distribution quantitative image is obtained by the Nakagami parametric extraction; and the two-dimensional cavitation distribution sequence images corresponding to different placing positions are transformed into the cavitation and cavitation concentration distribution quantitative three-dimensional image by the three-dimensional reconstruction algorithm; finally, by changing the cavitation energy incitation duration, a time-related cavitation and cavitation concentration quantitative three-dimensional spatial-temporal distribution image is obtained, whose time resolution is up to a few microseconds; by changing a time delay between the cavitation energy incitation and transmitting the wide beam by the array transducer, a time-related-dissipating cavitation and cavitation concentration quantitative three-dimensional spatial-temporal distribution image is obtained; by changing a time delay between pulsation and the cavitation energy incitation, a cavitation and cavitation concentration quantitative three-dimensional spatial-temporal distribution images corresponding to different time points within the pulsating cycle are obtained; by changing a cavitation energy value, an energy-related cavitation and cavitation concentration quantitative three-dimensional spatial-temporal distribution image is obtained; by changing a cavitation energy medium, a medium-related cavitation and cavitation concentration quantitative three-dimensional spatial-temporal distribution image is obtained.

BRIEF DESCRIPTION OF THE DRAWINGS

FIGS. 6-8 illustrate cavitation and cavitation concentration quantitative three-dimensional imaging results of the present invention when using a high-intensity focused ultrasound transducer for cavitation incitation in city water, wherein a pulse length of a high-intensity focused ultrasound is 10 us-200 ms, an electric power is 100 W, and arrows point to an ultrasound direction.

Element reference: 1-cavitation energy source, 2-power amplifier, 3-waveform generator, 4-all-digital ultrasonic equipment, 5-first three-dimensional mechanical scanner, 5'-second three-dimensional mechanical scanner, 6-array transducer, 7-water channel, 8-sound-absorbing material, 9-pulsating pump, 10-artificial vascular tissue phantom, 11-storage pool, 12-waste liquid pool, 13-latex tube.

DETAILED DESCRIPTION OF THE PREFERRED EMBODIMENT

Referring to the drawings and preferred embodiments, the present invention is further illustrated.

Figure 1:
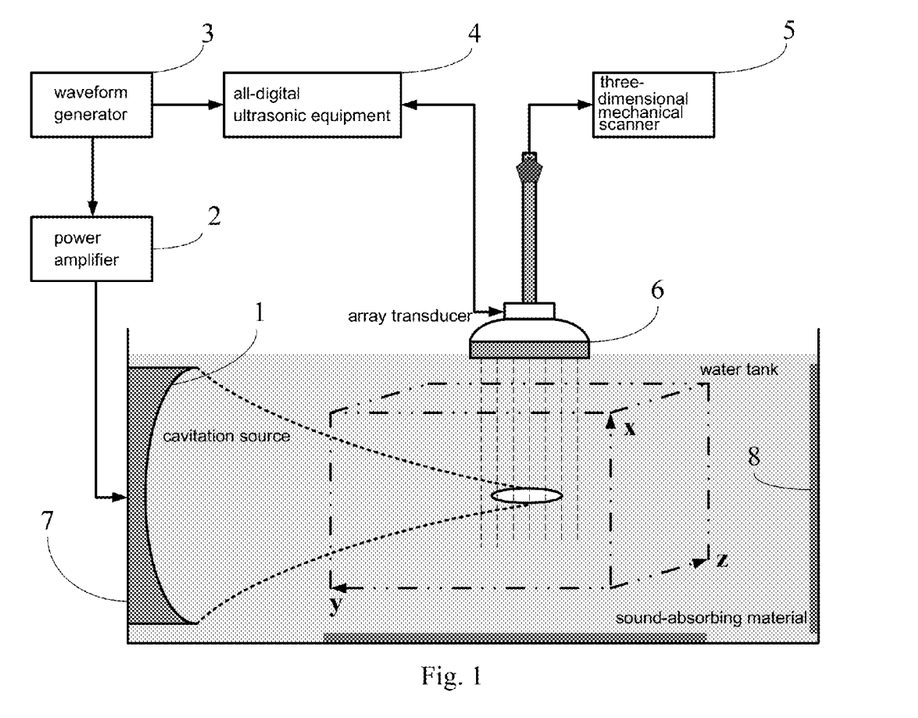
FIG. 1 is a sketch view of an array plane-by-plane wide beam cavitation detector of the present invention.

Referring to FIG. 1, an array plane-by-plane wide beam cavitation detector comprises a cavitation generator and a cavitation signal detector, wherein the cavitation generator comprises an energy source 1, a power amplifier 2 and a waveform generator 3 which controls a time sequence; the cavitation signal detector comprises a array transducer 6 which is programmable and transmits a wide beam and a parallel change data acquisition and storage unit of an all-digital ultrasonic equipment 4. A first channel of the waveform generator 3 drives the power amplifier 2, in such a manner that the energy source 1 generates an energy field. On one hand, waveform editing of the waveform generator 3 controls parameters such as an energy duration and a working mode of the energy source 1 with a time resolution of up to microsecond; one the other hand, a panel of the power amplifier 2 controls a value of the energy source 1. A second channel of the waveform generator 3 drives the all-digital ultrasonic equipment 4 for transmitting the wide beam and acquiring original cavitation radio frequency data, wherein transmitting and receiving parameters are set by programming the all-digital ultrasonic equipment 4. The first channel and the second channel of the waveform generator 3 enable time synchronization between the cavitation generator and the cavitation signal detector, or set a time delay therebetween according to requirements. After the cavitation is generated by the energy source 1 and the cavitation signal is acquired, the following steps are provided: waiting until a medium cavitation nuclei distribution backs to an initial state, controlling with a first three-dimensional mechanical scanner 5 for moving the array transducer 6 by one unit along a direction perpendicular to a placing direction of the array transducer 6, wherein the one unit is set by the first three-dimensional mechanical scanner 5; generating the cavitation again by cavitation energy source incitation with same parameters, and meanwhile transmitting the wide beam by the array transducer 6 for acquiring cavitation radio frequency data; repeating the above processes for obtaining a two-dimensional cavitation distribution image original radio frequency data collection corresponding to different placing positions along the direction perpendicular to the placing direction of the array transducer 6 with same cavitation energy source parameters. The above operation is provided in a water channel 7 whose bottom and side walls are provided with sound-absorbing materials 8.

Figure 2:
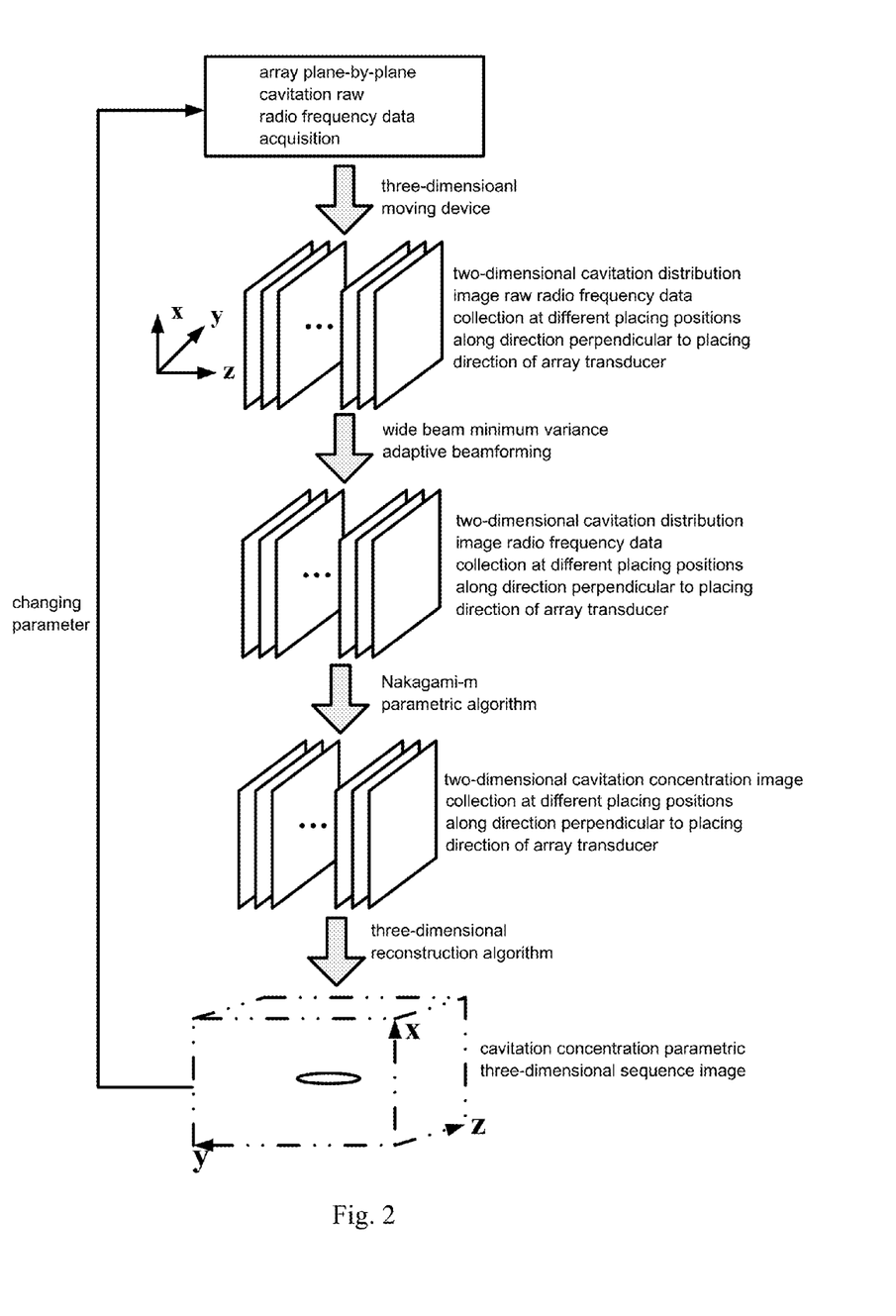
FIG. 2 is a flow chart of three-dimensional quantitative imaging for microsecond-resolution cavitation of the present invention.

Referring to FIG. 2, a three-dimensional quantitative imaging method for microsecond-resolution cavitation comprises steps of:

(1) using an array plane-by-plane wide beam for detecting the cavitation, wherein the programmable all-digital ultrasound equipment 4 transmits the wide beam for detecting the cavitation, so as to obtain the cavitation signal original radio frequency; then waiting until a medium cavitation nuclei distribution backs to an initial state, controlling with a first three-dimensional mechanical scanner 5 for moving the array transducer 6 by one unit along a direction perpendicular to a placing direction of the array transducer 6, wherein the one unit is set by the first three-dimensional mechanical scanner 5; generating the cavitation again by cavitation energy source incitation with same parameters, and meanwhile transmitting the wide beam by the array transducer 6 for acquiring cavitation radio frequency data; repeating the above processes for obtaining a two-dimensional cavitation distribution image original radio frequency data collection corresponding to different placing positions along the direction perpendicular to the placing direction of the array transducer 6 with same cavitation energy source parameters;

(2) processing two-dimensional cavitation original radio frequency data with wide beam minimum variance adaptive beamforming, so as to obtain a two-dimensional cavitation radio frequency data collection at different placing positions of the array transducer 6 along the direction perpendicular to the placing direction of the array transducer 6; then providing envelope demodulation, logarithmic compression and coordinate transformation for obtaining a two-dimensional cavitation distribution image collection;

(3) using Nakagami parametric imaging algorithm for quantitatively imaging the two-dimensional cavitation radio frequency data collection, and extracting cavitation concentration parameters for obtaining a two-dimensional cavitation concentration image collection at different placing positions of the array transducer 6 along the direction perpendicular to the placing direction of the array transducer 6;

(4) using a three-dimensional reconstruction algorithm for three-dimensionally reconstructing the sequence two-dimensional cavitation distribution images and two-dimensional cavitation concentration images at different placing positions of the array transducer 6 along the direction perpendicular to the placing direction of the array transducer 6, so as to obtain a three-dimensional cavitation distribution image and a three-dimensional cavitation concentration image under energy source incitation; and (5) changing parameters of the energy source 1 which generates the cavitation and a medium, and repeating the steps (1)-(4), for obtaining cavitation and cavitation concentration quantitation three-dimensional sequence images.

Figure 3:
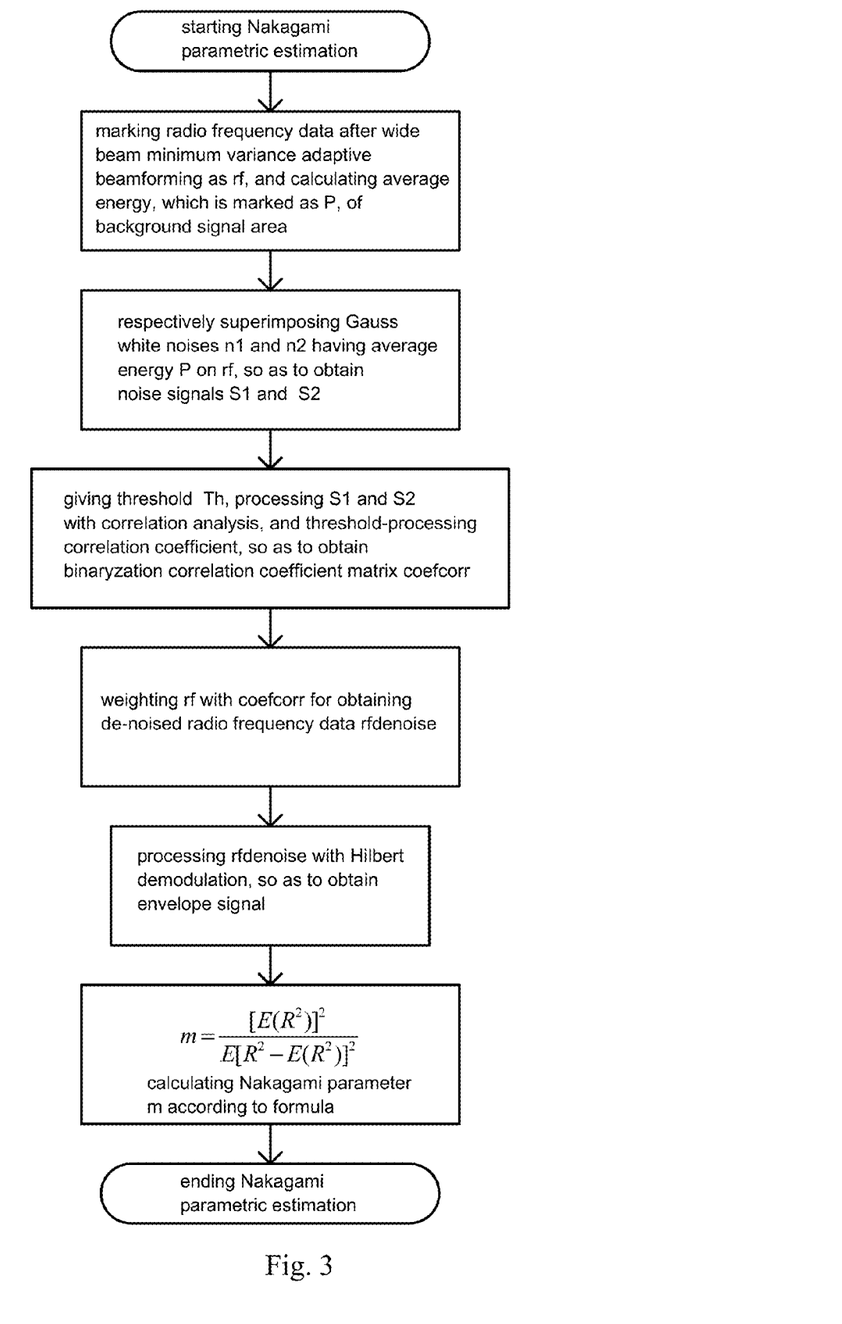
FIG. 3 is a flow chart of Nakagami parametric imaging of the present invention.

Referring to FIG. 3, a flow chart of the Nakagami parametric imaging algorithm is illustrated, comprising steps of:

(1) marking radio frequency data after the wide beam minimum variance adaptive beamforming as rf, and calculating an average energy, which is marked as P, of a background signal area;

(2) respectively superimposing random Gauss white noises having the average energy P on the rf, so as to obtain noise signals $S_1$ and $S_2$;

(3) giving a threshold Th, processing the $S_1$ and the $S_2$ with correlation analysis, and threshold-processing a correlation coefficient, so as to obtain a binaryzation correlation coefficient matrix $Coef_{corr}$;

(4) weighting the $Coef_{corr}$ obtained in the step (3) for obtaining de-noised radio frequency data $rf_{denoise}$:

$$rf_{denoise} = \begin{cases} rf, & corrcoef(S_1, S_2) > Th \\ 0, & corrcoef(S_1, S_2) \leq Th \end{cases}$$

(5) processing the $rf_{denoise}$ obtained in the step (4) with Hilbert demodulation, so as to obtain an envelope signal R;

wherein according to a Nakagami statistical model, a probability density function of the R is:

$$f(R) = \frac{2m^m R^{2m-1}}{\Gamma(m)\Omega^m} \exp\left(-\frac{m}{\Omega}R^2\right) U(R)$$

wherein $\Gamma(\square)$ and $U(\square)$ are respectively a gamma function and a unit step function, and m and $\Omega$ are respectively a Nakagami parameter and a scale parameter of the Nakagami statistical model; and (6) calculating the Nakagami parameter with $$m = \frac{[E(R^2)]^2}{E[R^2 - E(R^2)]^2}.$$

Figure 4:
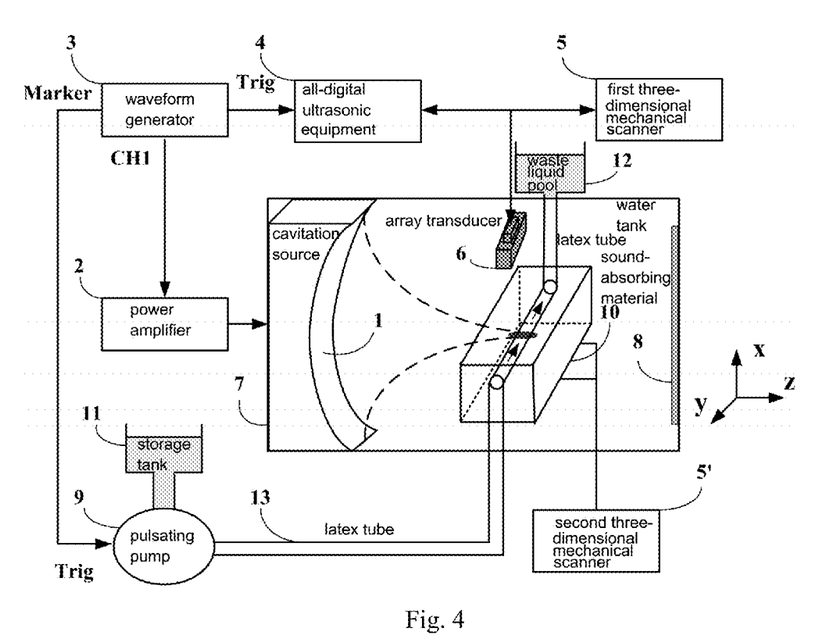
FIG. 4 is a sketch view of a pulsating flow microsecond cavitation imaging device of the present invention.

Referring to FIG. 4, a pulsating flow microsecond-resolution cavitation three-dimensional quantitative image device comprises a pulsating flow device, a cavitation generator and a cavitation signal detector, wherein the pulsating flow device comprises a pulsating pump 9, an artificial vascular tissue phantom 10, and a waveform generator 3 for triggering; the cavitation generator comprises an energy source 1, a power amplifier 2 and the waveform generator 3 which controls a time sequence; the cavitation signal detector comprises a array transducer 6 which is programmable and transmits a wide beam and a parallel change data acquisition and storage unit of an all-digital ultrasonic equipment 4. A first channel of the waveform generator 3 drives the power amplifier 2, in such a manner that the energy source 1 generates an energy field. On one hand, waveform editing of the waveform generator 3 controls parameters such as an energy duration and a working mode of the energy source 1 with a time resolution of up to microsecond; one the other hand, a panel of the power amplifier 2 controls a value of the energy source 1. A second channel of the waveform generator 3 drives the all-digital ultrasonic equipment 4 for transmitting the wide beam and acquiring original cavitation radio frequency data, wherein transmitting and receiving parameters are set by programming the all-digital ultrasonic equipment 4. A Maker channel of the waveform generator 3 triggers the pulsating pump 9. The first channel, the second channel and the Maker channel of the waveform generator 3 enable time synchronization between the pulsating flow device, the cavitation generator and the cavitation signal detector, or set a time delay therebetween according to requirements. The following steps are provided: connecting two ends of a pipeline of the artificial vascular tissue phantom 10 to a latex tube 13, and connecting to the pulsating pump 9; moving liquid form a storage pool 11 to a waste liquid pool 12 for simulating a pulsating blood flow; connecting the artificial vascular tissue phantom 10 to a second three-dimensional mechanical scanner 5', placing in a cavitation source effective area by three-dimensional movements, and generating cavitation inside the pipeline of the artificial vascular tissue phantom 10; using a Doppler mode of the all-digital ultrasonic equipment 4, testing Doppler spectrums under different parameters of the pulsating pump 9, and recording a pulsating cycle and pattern for editing a synchronous waveform time sequence of the waveform generator 3; wherein the programmable array transducer 6 of the all-digital ultrasonic equipment 4 is connected to the first three-dimensional mechanical scanner 5; after the cavitation is generated by the energy source 1 and the cavitation signal is acquired, waiting until a medium cavitation nuclei distribution backs to an initial state, controlling with the first three-dimensional mechanical scanner 5 for moving the array transducer 6 by one unit along a direction perpendicular to a placing direction of the array transducer 6, wherein the one unit is set by the first three-dimensional mechanical scanner 5; generating the cavitation again by cavitation energy source incitation with same parameters, and meanwhile transmitting the wide beam by the array transducer 6 for acquiring cavitation radio frequency data; repeating the above processes for obtaining a two-dimensional cavitation distribution image original radio frequency data collection corresponding to different placing positions along the direction perpendicular to the placing direction of the array transducer 6 with same cavitation energy source parameters. The above operation is provided in a water channel 7 whose bottom and side walls are provided with sound-absorbing materials 8.

Figure 5:
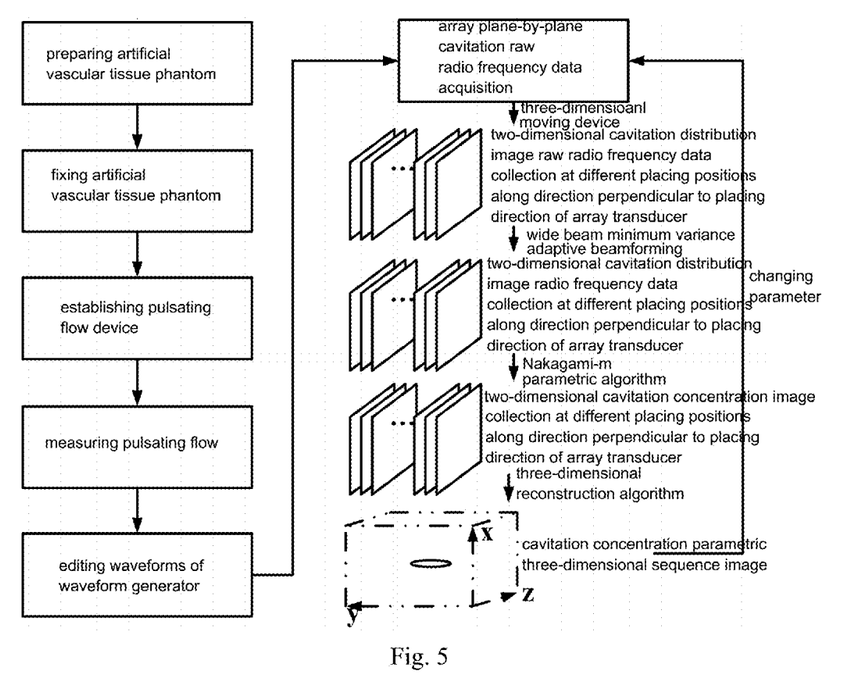
FIG. 5 is a flow chart of the pulsating flow microsecond cavitation three-dimensional quantitative imaging of the present invention.

Referring to FIG. 5, a pulsating flow microsecond-resolution cavitation three-dimensional quantitative image method comprises steps of:

(1) preparing the artificial vascular tissue phantom 10 by pouring a gel solution into a mould, after cooling and solidifying, slowly taking out a pipe for forming the pipeline inside the solidified gel; (2) connecting the artificial vascular tissue phantom 10 to a second three-dimensional mechanical scanner 5', placing in a cavitation source effective area by three-dimensional movements, and generating cavitation inside the pipeline of the artificial vascular tissue phantom 10; (3) establishing the pulsating flow device by connecting two ends of a pipeline of the artificial vascular tissue phantom 10 to the latex tube 13, and connecting to the pulsating pump 9; moving liquid form a storage pool 11 to a waste liquid pool 12 for simulating a pulsating blood flow; (4) measuring the pulsating flow, wherein the liquid in the storage pool 11 is a normal saline contrast agent micro bubble solution; setting the all-digital ultrasonic equipment 4 to the Doppler mode, and recording the pulsating cycle and pattern; (5) according to the pulsating cycle recorded, editing waveforms of the first channel, the second channel and the Marker channel of the waveform generator, and respectively inputting into the power amplifier 2 for cavitation incitation by the energy source 1, to the all-digital ultrasonic equipment 4 for controlling the array transducer 6 for transmitting and receiving a plane wave signal, and to the pulsating pump 9 for controlling a time delay between each time point with the pulsating cycle and the energy source 1; (6) using an array plane-by-plane wide beam for detecting the cavitation, wherein the programmable all-digital ultrasound equipment 4 transmits the wide beam for detecting the cavitation, so as to obtain the cavitation signal original radio frequency; then waiting until a medium cavitation nuclei distribution backs to an initial state, controlling with a first three-dimensional mechanical scanner 5 for moving the array transducer 6 by one unit along a direction perpendicular to a placing direction of the array transducer 6, wherein the one unit is set by the first three-dimensional mechanical scanner 5; generating the cavitation again by cavitation energy source incitation with same parameters, and meanwhile transmitting the wide beam by the array transducer 6 for acquiring cavitation radio frequency data; repeating the above processes for obtaining sequence two-dimensional cavitation distribution image original radio frequency data corresponding to different placing positions along the direction perpendicular to the placing direction of the array transducer 6 with same cavitation energy source parameters; (7) processing sequence two-dimensional cavitation original radio frequency data with wide beam minimum variance adaptive beamforming, so as to obtain sequence two-dimensional cavitation radio frequency data at different placing positions of the array transducer 6 along the direction perpendicular to the placing direction of the array transducer 6; then providing envelope demodulation, logarithmic compression and coordinate transformation for obtaining sequence two-dimensional cavitation distribution images; (8) using a Nakagami parametric imaging algorithm for quantitatively imaging the sequence two-dimensional cavitation radio frequency data, and extracting cavitation concentration parameters for obtaining sequence two-dimensional cavitation concentration image at different placing positions of the array transducer 6 along the direction perpendicular to the placing direction of the array transducer 6; (9) using a three-dimensional reconstruction algorithm for three-dimensionally reconstructing the sequence two-dimensional cavitation distribution images and two-dimensional cavitation concentration images at different placing positions of the array transducer 6 along the direction perpendicular to the placing direction of the array transducer 6, so as to obtain a three-dimensional cavitation distribution image and a three-dimensional cavitation concentration image under energy source incitation; and (10) changing parameters of the energy source 1 which generates the cavitation and a medium, and repeating the steps (1)-(4), for obtaining cavitation and cavitation concentration quantitation three-dimensional sequence images.

Preferred embodiment 1: a medium is city water, a pulse length of a high-intensity focused ultrasound is 10 us-200 ms, and an electric power is 100 W, wherein cavitation bubble groups generated under above conditions are processed with cavitation and cavitation concentration quantitative three-dimensional imaging, comprising steps of:

(1) using an experiment device as shown in FIG. 1, and pouring city water into a water channel; then mounting a high-intensity focused ultrasound transducer on a side wall of the water channel, and transmitting a wide beam by a Sonix-Touch all-digital ultrasound equipment for detecting cavitation micro bubbles; placing an array transducer along a high-intensity focused ultrasound transmitting direction, in such a manner that a center thereof is corresponding to a focal region of the high-intensity focused ultrasound transducer; and synchronizing both through a double-channel arbitrary waveform generator AWG420; (2) setting the pulse length of the high-intensity focused ultrasound (HIFU) to 10 us-200 ms through a waveform generator, setting the electric power to 100 W through a power amplifier, and setting a time delay between a first channel which triggers the power amplifier and a second channel which triggers the Sonix-Touch all-digital ultrasound equipment to 1 ms by waveform editing; (3) using an array plane-by-plane wide beam for detecting the cavitation, using a three-dimensional mechanical scanner Multiscan 5800 for moving along a direction perpendicular to a placing direction of the array transducer, wherein a moving unit is set to 0.5 mm, for obtaining sequence two-dimensional cavitation original radio frequency data at different placing positions; (4) processing the sequence two-dimensional cavitation original radio frequency data with wide beam minimum variance adaptive beamforming, so as to obtain sequence two-dimensional cavitation radio frequency data at different placing positions; (5) for the sequence two-dimensional cavitation radio frequency data, on one hand, using envelope demodulation, logarithmic compression and coordinate transformation for obtaining sequence two-dimensional cavitation distribution images; on the other hand, using a Nakagami parametric imaging algorithm for obtaining sequence two-dimensional cavitation concentration distribution images; and (6) using a three-dimensional reconstruction algorithm for respectively reconstructing the sequence two-dimensional cavitation distribution image and the cavitation concentration distribution image with a HIFU pulse length of 20 ms, so as to obtain a three-dimensional cavitation distribution image and a three-dimensional cavitation concentration image in the city water.

Figure 6:
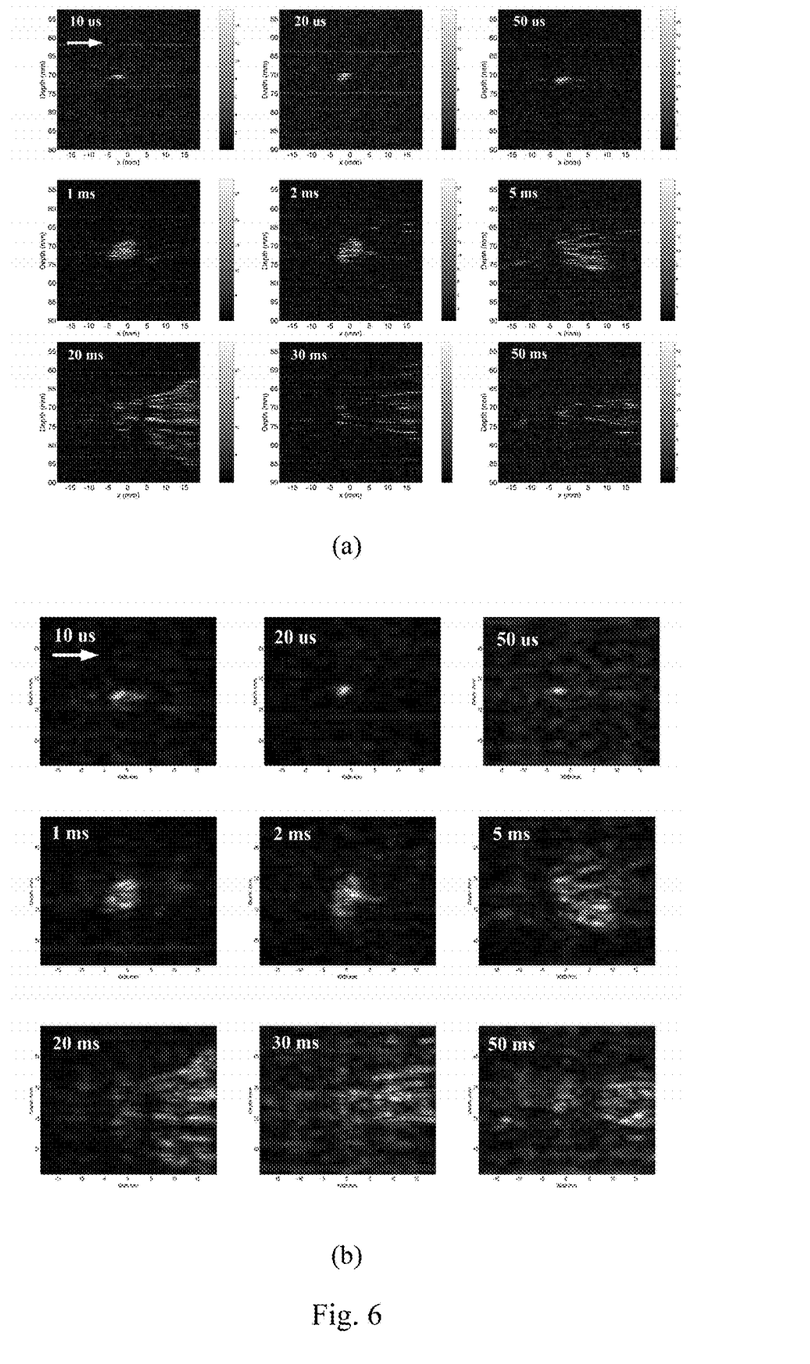
FIG. 6(a) is a two-dimensional spatial-temporal distribution cavitation image.
FIG. 6(b) is a two-dimensional cavitation micro bubble concentration quantitative image.
Figure 7:
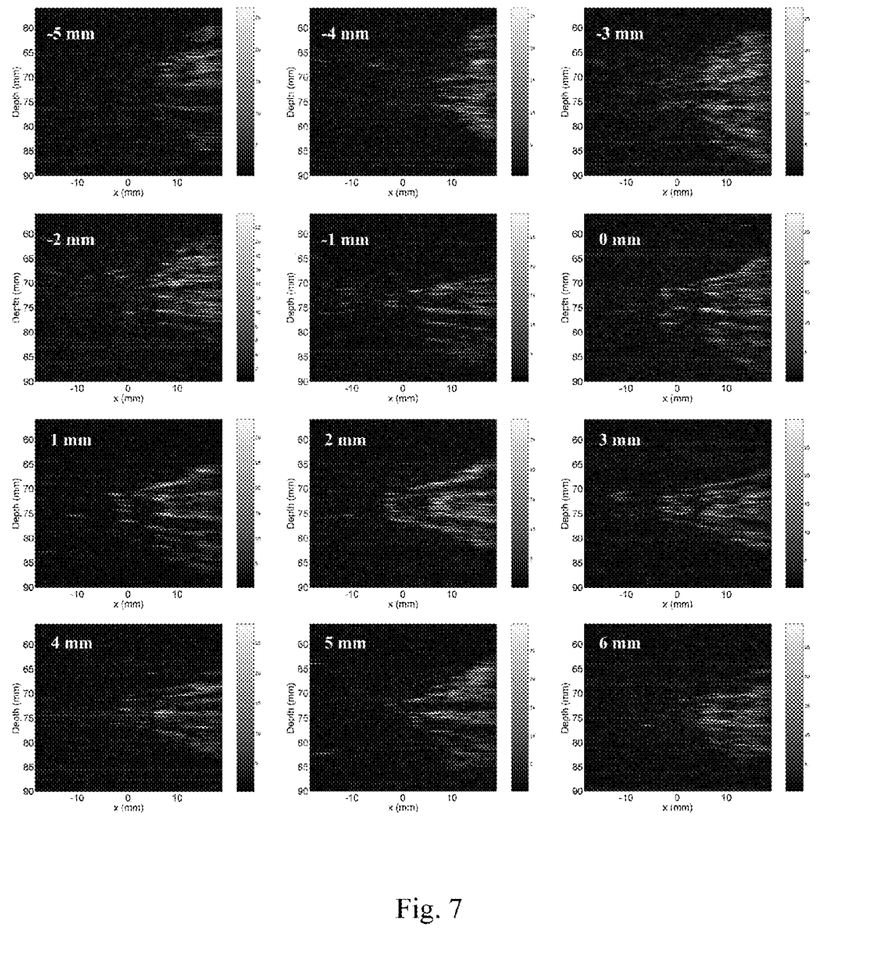
FIG. 7 illustrates space sequence cavitation imaging by moving an array transducer from −5 mm position to 6 mm position when the pulse length is 20 ms.
Figure 8:
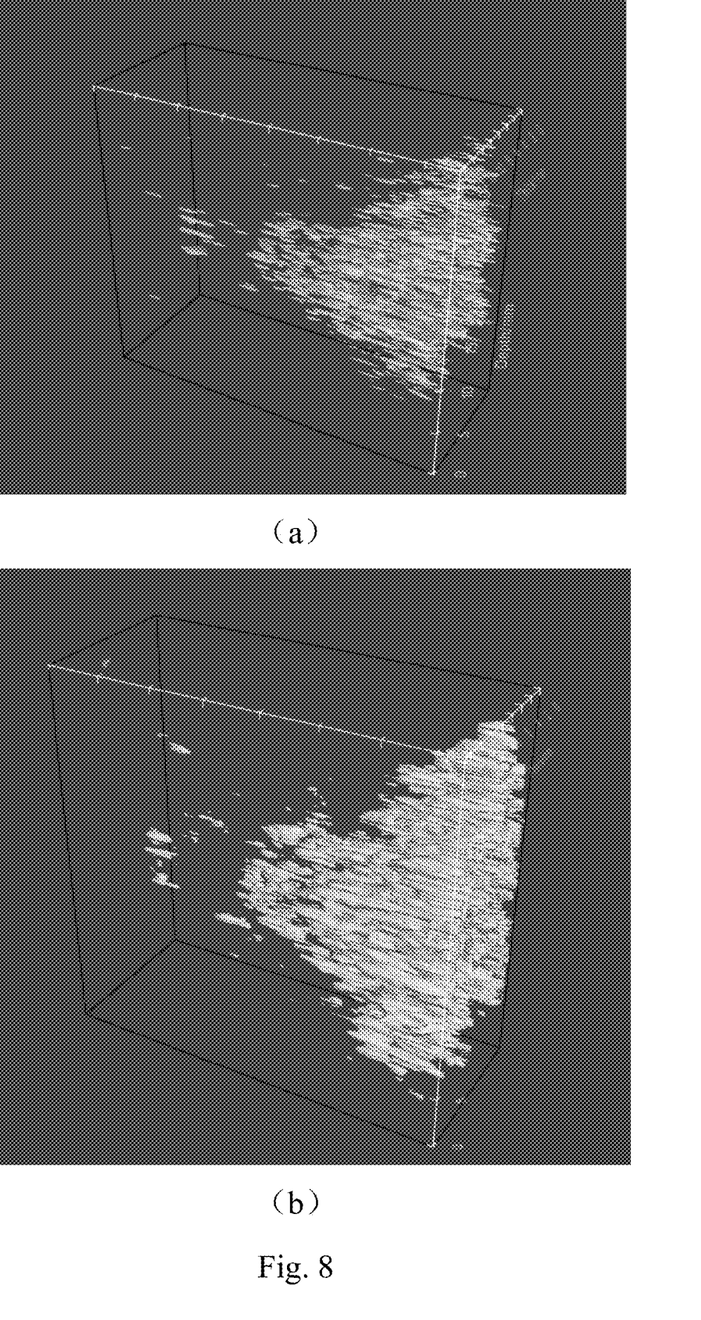
FIG. 8(a) is a three-dimensional cavitation image when the pulse length is 20 ms.
FIG. 8(b) is a three-dimensional cavitation micro bubble concentration image when the pulse length is 20 ms.

When the array transducer is at 0 mm, cavitation spatial-temporal and cavitation concentration spatial-temporal distribution results with the HIFU pulse length of 10 us-200 ms are shown in FIG. 6. According to analysis, the cavitation bubbles appear in the focal region because a sound pressure in the focal region is highest. However, a center position of the bubble group is not precisely at a focal point of 0 mm position. Actually, the center position is slightly behind the focal region because a radially force works on the cavitation micro bubbles, in such a manner that the cavitation micro bubbles move along a sound transmitting direction. When the pulse length is 5 ms, the cavitation bubble group will form a branch structure behind the focal region and will grow bigger; when the pulse length is 200 ms, a sound radical force will to too large to the branch structure of the cavitation bubble group. FIG. 7 illustrates a cavitation bubble group sectional distribution after moving the array transducer from −5 mm position to 6 mm position when the pulse length is 20 ms. FIG. 7 also illustrates a space sequence cavitation distribution after moving the array transducer from −5 mm position to 6 mm position when the pulse length is 20 ms. FIG. 8 illustrates a three-dimensional cavitation image (a) and a three-dimensional cavitation micro bubble concentration image (b) when the pulse length is 20 ms.

Preferred embodiment 2: under a pulsating flow condition, a pulse length of a high-intensity focused ultrasound is 20 us, an electric power is 100 W, a pulsating frequency is 80 times per second, a flow rate is 5 cm/s, and a pipe diameter is 4 mm; wherein cavitation bubble groups generated under above conditions are processed with cavitation and cavitation concentration quantitative three-dimensional imaging, comprising steps of:

(1) preparing an agar gelatin artificial vascular tissue phantom by mixing, heating and stirring agar (3%), gelatin (12%) and de-gassed water (85%) until being completely dissolved, putting into a de-gassing tank and de-gassing for 30 min, then pouring into a mould, after cooling and solidifying, slowly taking out a pipe for forming a pipeline; and connecting two sides of the pipeline to a latex tube and to a pulsating pump, wherein the pulsating pump moves liquid from a storage tank to a waste water tank for forming a pulsating flow inside the pipeline;

(2) using an experiment device as shown in FIG. 4, and pouring city water into a water channel; then mounting a high-intensity focused ultrasound transducer on a side wall of the water channel, and transmitting a wide beam by a Sonix-Touch all-digital ultrasound equipment for detecting cavitation micro bubbles; placing an array transducer along a high-intensity focused ultrasound transmitting direction, and connecting the agar gelatin artificial vascular tissue phantom to a three-dimensional moving device, so as to focusing the high-intensity focused ultrasound inside the pipeline, for generating cavitation inside the pipeline;

(3) setting a pulsating frequency to 80 times per second and a flow rate to 5 cm/s, wherein the liquid in the storage pool is a normal saline contrast agent micro bubble solution; setting a Sonix-Touch all-digital ultrasonic equipment to a Doppler mode, and recording a Doppler spectrum under such pulsating parameters and analyzing a pulsating cycle and pattern, so as to edit a waveform of a waveform generator AWG420; respectively inputting a CH1, a CH2 and a Marker channel into the power amplifier, the Sonix-Touch and the pulsating pump, for achieving synchronization therebetween;

(4) fixing the array transducer, and using an array plane-by-plane wide beam for detecting the cavitation; then changing a time delay between the pulsating pump and the power amplifier by respectively setting to 0-12 ms with an unit time of 1 ms; stopping for 2s each time, in such a manner that liquid cavitation nuclei distribution backs to an initial state; and obtaining sequence two-dimensional cavitation distribution image original radio frequency data at different time points within the pulsating cycle;

(5) using a three-dimensional mechanical scanner Multi-scan 5800 for moving along a direction perpendicular to a placing direction of the array transducer, wherein a moving unit is set to 1 mm, for obtaining sequence two-dimensional cavitation original radio frequency data at different placing positions;

(6) beamforming the sequence two-dimensional cavitation distribution image original radio frequency data at different time points within the pulsating cycle and the sequence two-dimensional cavitation original radio frequency with a wide beam minimum variance adaptive beamforming algorithm, so as to obtain sequence two-dimensional cavitation radio frequency data at different time points within the pulsating cycle and different placing positions;

(7) for the sequence two-dimensional cavitation radio frequency data, on one hand, using envelope demodulation, logarithmic compression and coordinate transformation for obtaining sequence two-dimensional cavitation distribution images at different time points within the pulsating cycle and different placing positions; on the other hand, using a Nakagami parametric imaging algorithm for obtaining sequence two-dimensional dimensional cavitation concentration distribution images at different time points within the pulsating cycle and different placing positions; and (8) using a three-dimensional reconstruction algorithm for respectively reconstructing the sequence two-dimensional cavitation distribution image and the cavitation concentration distribution image, so as to obtain a three-dimensional cavitation distribution image and a three-dimensional cavitation concentration image when the pulse length of the high-intensity focused ultrasound is 20 us and the electric power is 100 W.

Figure 9:
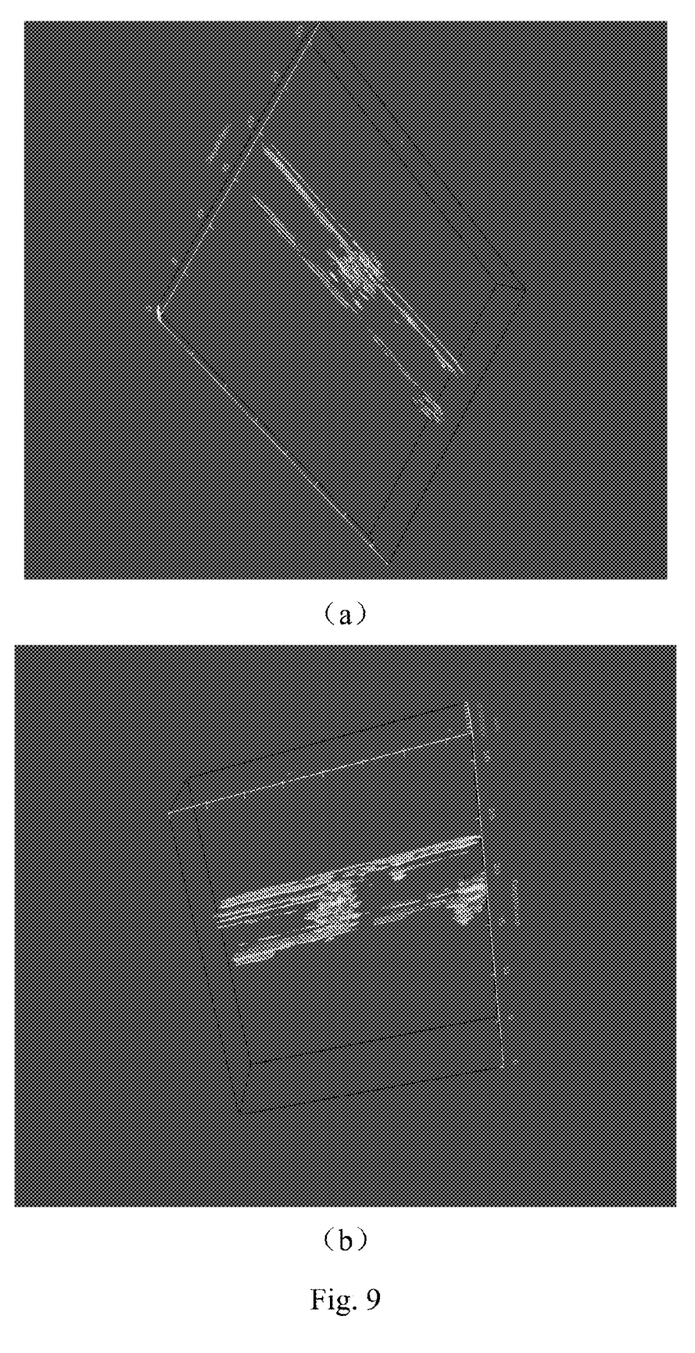
FIG. 9 illustrates cavitation and cavitation concentration quantitative three-dimensional imaging results of the present invention when using the high-intensity focused ultrasound transducer for cavitation incitation in a pulsating flow, wherein the pulse length of the high-intensity focused ultrasound is 20 us, the electric power is 100 W, and arrows point to the ultrasound direction.

FIG. 9 illustrates the three-dimensional cavitation image (a) and the three-dimensional cavitation concentration image (b) under the conditions of the preferred embodiment 2. It is concluded that the pipeline of the artificial vascular tissue phantom is full of the cavitation micro bubbles, and the cavitation micro bubbles extend to two ends of the pipeline.

Principles are as follows: after each wide beam detection, moving an array transducer by one unit; waiting until a cavitation nuclei distribution backs to an initial state, then detecting the cavitation by the wide beam detection with same cavitation energy incitation, so as to obtain a spatial two-dimensional cavitation original radio frequency data collection corresponding to different placing positions of the array transducer; then changing time delays between a cavitation energy source duration, energy source incitation and the wide beam transmitted by the array transducer, and changing a time delay between the pulsating pump and energy source incitation, so as to obtain time sequence two-dimensional cavitation original radio frequency data; and obtaining a microsecond-resolution cavitation three-dimensional spatial-temporal distribution image and a cavitation micro bubble concentration quantitative image by the combining the wide beam minimum variance adaptive beamforming, the Nakagami parametric imaging, and the three-dimensional reconstruction algorithm. The method combines array plane-by-plane wide beam cavitation detection, the wide beam minimum variance adaptive beamforming, and the Nakagami parametric imaging algorithm, which not only has imaging characteristics such as a high spatial resolution and a high signal-noise ratio, but also achieves microsecond-resolution cavitation three-dimensional spatial-temporal distribution imaging and cavitation micro bubble concentration quantitative imaging under the static-state free field and the pulsating flow conditions. The method has a potential to be a three-dimensional cavitation imaging standard method which is similar to acoustic field measurement.

What is claimed is:

1. A three-dimensional cavitation quantitative imaging method for a microsecond-resolution cavitation spatial-temporal distribution, comprising steps of: using a wide beam to detect cavitation activity for two-dimensional cavitation raw radio frequency data obtained; after cavitation detection by the wide beam, moving an array transducer for the wide beam detection by one unit perpendicular to a placing direction of the array transducer; waiting until a cavitation nuclei distribution returns to an original state thereof, then detecting the cavitation by the wide beam detection with the same cavitation energy incitation, so as to obtain a spatial series of two-dimensional cavitation raw radio frequency data with the array transducer placed at different unit positions; and then obtaining a three-dimensional cavitation image and a cavitation micro bubble concentration quantitative three-dimensional image by combining wide beam minimum variance adaptive beamforming, Nakagami parametric imaging, and a three-dimensional reconstruction algorithm.

2. The three-dimensional cavitation quantitative imaging method, as recited in claim 1, wherein a cavitation generator comprises an energy source and a synchronous signal generator; a cavitation detector comprises the array transducer which is programmable and transmits the wide beam, and a parallel channel data acquisition and storage unit; wherein the synchronous signal generator generates a synchronous signal so as to respectively control the energy source and the array transducer; the energy source generates energy which induces cavitation bubbles, and the energy generated by the energy source is continuously adjustable; the array transducer transmits the wide beam for detecting the cavitation, and a cavitation echo signal obtained is acquired and stored by the parallel channel data acquisition and storage unit.

3. The three-dimensional cavitation quantitative imaging method, as recited in claim 1, specifically comprising steps of: beamforming the two-dimensional cavitation raw radio frequency data by a wide beam minimum variance adaptive beamforming algorithm, so as to obtain a spatial series of the two-dimensional cavitation radio frequency data at the different placing positions of the array transducer; and then obtaining a spatial series of two-dimensional cavitation distribution images based on the spatial series of the two-dimensional cavitation radio frequency data; and as the spatial series of beamformed radio frequency data in three-dimensional space are required, using the three-dimensional reconstruction algorithm to reconstruct the three-dimensional cavitation distribution image, so as to obtain the three-dimensional cavitation image.

4. The three-dimensional cavitation quantitative imaging method, as recited in claim 1, specifically comprising steps of: beamforming the two-dimensional cavitation original radio frequency data by a wide beam minimum variance adaptive beamforming algorithm, so as to obtain a spatial series of the two-dimensional cavitation radio frequency data at the different placing positions of the array transducer; processing the spatial series of the two-dimensional cavitation radio frequency data with Nakagami parametric extraction, so as to obtain a spatial series of two-dimensional cavitation concentration quantitative images; and as the spatial series of the two-dimensional cavitation concentration quantitative images in three-dimensional space are required, using the three-dimensional reconstruction algorithm to reconstruct the three-dimensional cavitation concentration quantitative image, so as to obtain the cavitation micro bubble concentration quantitative three-dimensional image.

5. The three-dimensional cavitation quantitative imaging method, as recited in claim 4, wherein the Nakagami parametric extraction comprises steps of:
1) de-noising two-dimensional cavitation radio frequency data rf:
a) selecting a background signal area with a certain size, and calculating an average energy P of the background signal area;
b) respectively superimposing a first random Gauss white noise $n_1$ and a second random Gauss white noise $n_2$, both having the average energy P, on the rf, so as to obtain $S_1$ and $S_2$; and
c) calculating a correlation coefficient of the $S_1$ and the $S_2$, and giving a threshold Th; threshold-processing the correlation coefficient and then weighting with the rf for obtaining $rf_{denoise}$:

$$rf_{denoise} = \begin{cases} rf, & corrcoef(S_1, S_2) > Th \\ 0, & corrcoef(S_1, S_2) \le Th \end{cases} \quad (1)$$

wherein corrcoef ($S_1$, $S_2$) is the correlation coefficient of the $S_1$ and the $S_2$;
2) processing the $rf_{denoise}$ with Hilbert demodulation, so as to obtain an envelope signal R; and
3) calculating a Nakagami parameter:

$$m = \frac{[E(R^2)]^2}{E[R^2 - E(R^2)]^2} \quad (3)$$

wherein E (□) represents a statistical mean.

6. The three-dimensional cavitation quantitative imaging method, as recited in claim 1, wherein by changing a cavitation energy incitation duration, temporal evolutions of three-dimensional cavitation image and temporal evolutions of cavitation micro bubble concentration quantitative three-dimensional image are obtained; by changing a power of the cavitation energy source, an energy-related three-dimensional cavitation image and an energy-related cavitation micro bubble concentration quantitative three-dimensional image are obtained; by changing a time delay between the cavitation energy incitation and transmitting the wide beam by the array transducer, a dissolving process of three-dimensional cavitation image and a dissolving process of cavitation micro bubble concentration quantitative three-dimensional image are obtained; by changing a medium where the cavitation energy source is exposed, a medium-related three-dimensional cavitation image and a medium-related cavitation micro bubble concentration quantitative three-dimensional image are obtained.

* * * * *